(12) United States Patent
Lee et al.

(10) Patent No.: US 6,972,422 B2
(45) Date of Patent: Dec. 6, 2005

(54) METHOD FOR MEASURING PARTICLES IN GLASS SUBSTRATE

(75) Inventors: Chang Ha Lee, Gyeongsangbuk-do (KR); Taek Cheon Kim, Gyeongsangbuk-do (KR); Suk Joon Kim, Gyeongsangbuk-do (KR); Ki Nam Kim, Gyeongsangbuk-do (KR); Ga Hyun Kim, Gyeongsangbuk-do (KR); Ji Hwa Jung, Gyeongsangbuk-do (KR)

(73) Assignee: Samsung Corning Precision Glass Co., Ltd., Gyeongsangbuk-do (KR)

( * ) Notice: Subject to any disclaimer, the term of this patent is extended or adjusted under 35 U.S.C. 154(b) by 81 days.

(21) Appl. No.: 10/816,818

(22) Filed: Apr. 5, 2004

(65) Prior Publication Data

US 2005/0116150 A1 Jun. 2, 2005

(30) Foreign Application Priority Data

Nov. 28, 2003 (KR) .................. 10-2003-0085622

(51) Int. Cl.⁷ .......................................... G01N 21/88
(52) U.S. Cl. .......................... 250/559.41; 250/559.46; 356/239.1; 356/237.3
(58) Field of Search ................. 250/559.4, 559.41, 250/559.42, 559.44, 559.45, 559.46, 559.47, 250/559.48; 356/239.1, 239.2, 239.7, 237.3

(56) References Cited

U.S. PATENT DOCUMENTS

2003/0122731 A1 * 7/2003 Miyake .................. 345/1.1
2005/0041243 A1 * 2/2005 Choo et al. ............. 356/239.1

* cited by examiner

Primary Examiner—Kevin Pyo
(74) Attorney, Agent, or Firm—Bacon & Thomas PLLC

(57) ABSTRACT

Particles in a glass substrate are measured by executing following steps: sequentially conveying a plurality of glass substrates; scanning with a camera a unit area of a glass substrate in a direction of a travel path of the glass substrate and storing particle information thereof; shifting the camera to a position corresponding to a next unit area for a succeeding glass substrate; storing information on the particles in the unit area of the succeeding glass substrate obtained by scanning the glass substrate; estimating whether a sum of the respective scanned unit areas is within an allowed limit of an area of a glass substrate; and returning to the third step if an answer from the fifth step is "No" or storing information on the particles in the entire glass substrate if the answer is "Yes".

5 Claims, 6 Drawing Sheets

METHOD FOR MEASURING PARTICLES IN GLASS SUBSTRATE

FIELD OF THE INVENTION

The present invention relates to a method for measuring particles in a glass substrate; and, more particularly, to a method capable of providing sampling information on particles in a glass substrate without interrupting the process line of the cleaned glass substrate.

BACKGROUND OF THE INVENTION

Generally, a glass substrate used in manufacturing a flat display such as a TFT-LCD (thin film transistor-liquid crystal display), a PDP (plasma display panel), an EL (electro luminescence) and the like is formed by molding and then cutting a molten glass melted in a glass melting furnace to meet an initial product standard, which is then coated with a protective film on a surface thereof.

Unlike a surface defect inspection of such glass substrate, which employs a general vision system, a method for measuring the number of particles present in such a glass substrate employs a high precision laser sensor, which takes a substantial amount of time to perform. Accordingly, a glass substrate undergoing such a time consuming process is taken off the process line, and moreover loading of the glass substrate for such process is non-automated and is done manually.

Such a manual operation of the glass substrate for measuring particles present therein requires a cleaning room with a large interior space. Furthermore, under such process, obtaining and storing of particles data are carried out manually, further exacerbating the time issue and causing great inconvenience to an operator.

Moreover, when dealing with a glass substrate of considerable size, loading thereof becomes problematic and a loading device is required.

SUMMARY OF THE INVENTION

It is, therefore, an object of the present invention to provide a method for measuring particles in a glass substrate capable of providing sampling information on the particles in a glass substrate without interruption in a process line; utilizing a clean room space efficiently; and performing an inspection of a large-sized glass substrate.

In accordance with a preferred embodiment of the present invention, there is provided a method for measuring particles in a glass substrate, including the steps of: (a) sequentially conveying a plurality of glass substrates; (b) scanning with a camera a unit area of a glass substrate in a direction of a travel path of the glass substrate and storing particle information thereof, wherein the camera is placed above the travel path of the glass substrates and a scan width thereof is preset; (c) shifting the camera in a direction perpendicular to the travel path of the glass substrate to a position corresponding to a next unit area for a succeeding glass substrate; (d) storing information on the particles in the unit area of the succeeding glass substrate obtained by scanning the glass substrate using the shifted camera; (e) estimating whether a sum of the respective scanned unit areas is within an allowed limit of an area of a glass substrate; and (f) returning to step (c) if an answer from step (e) is "No" or storing information on the particles in the entire glass substrate obtained by summing up the information on the particles in the respective scanned unit areas if the answer is "Yes".

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Figure 1A:
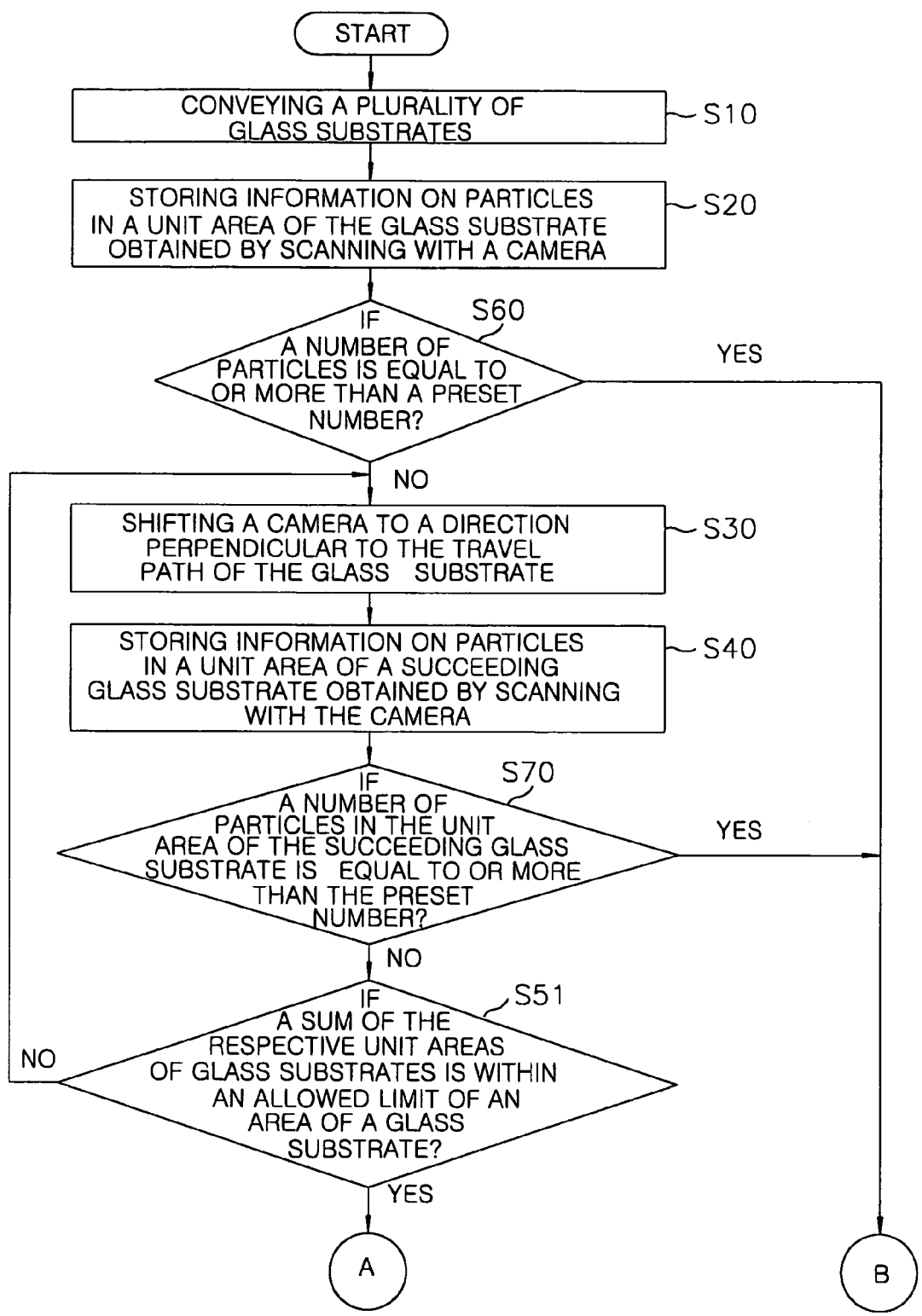
FIGS. 1A and 1B present a flow chart showing a method for measuring particles in a glass substrate in accordance with the present invention.
Figure 1B:
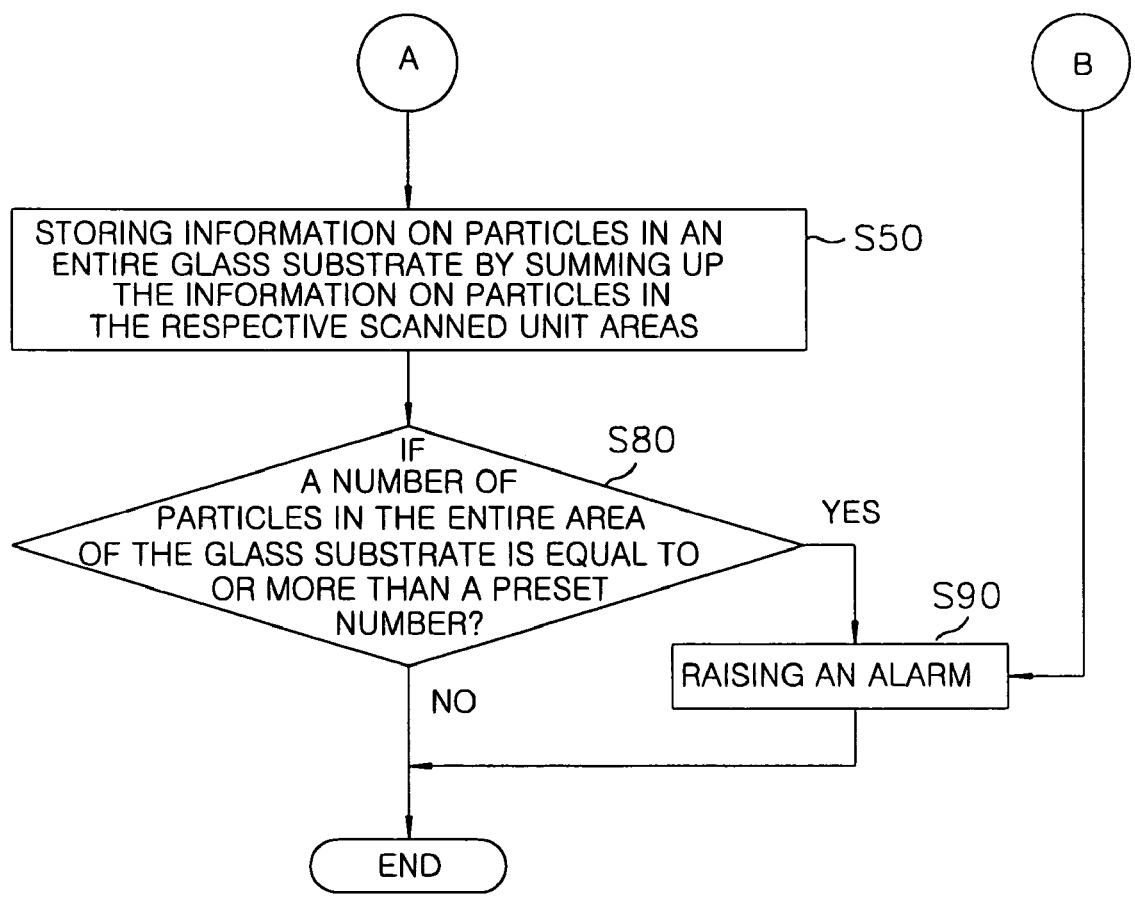
Figure 2:
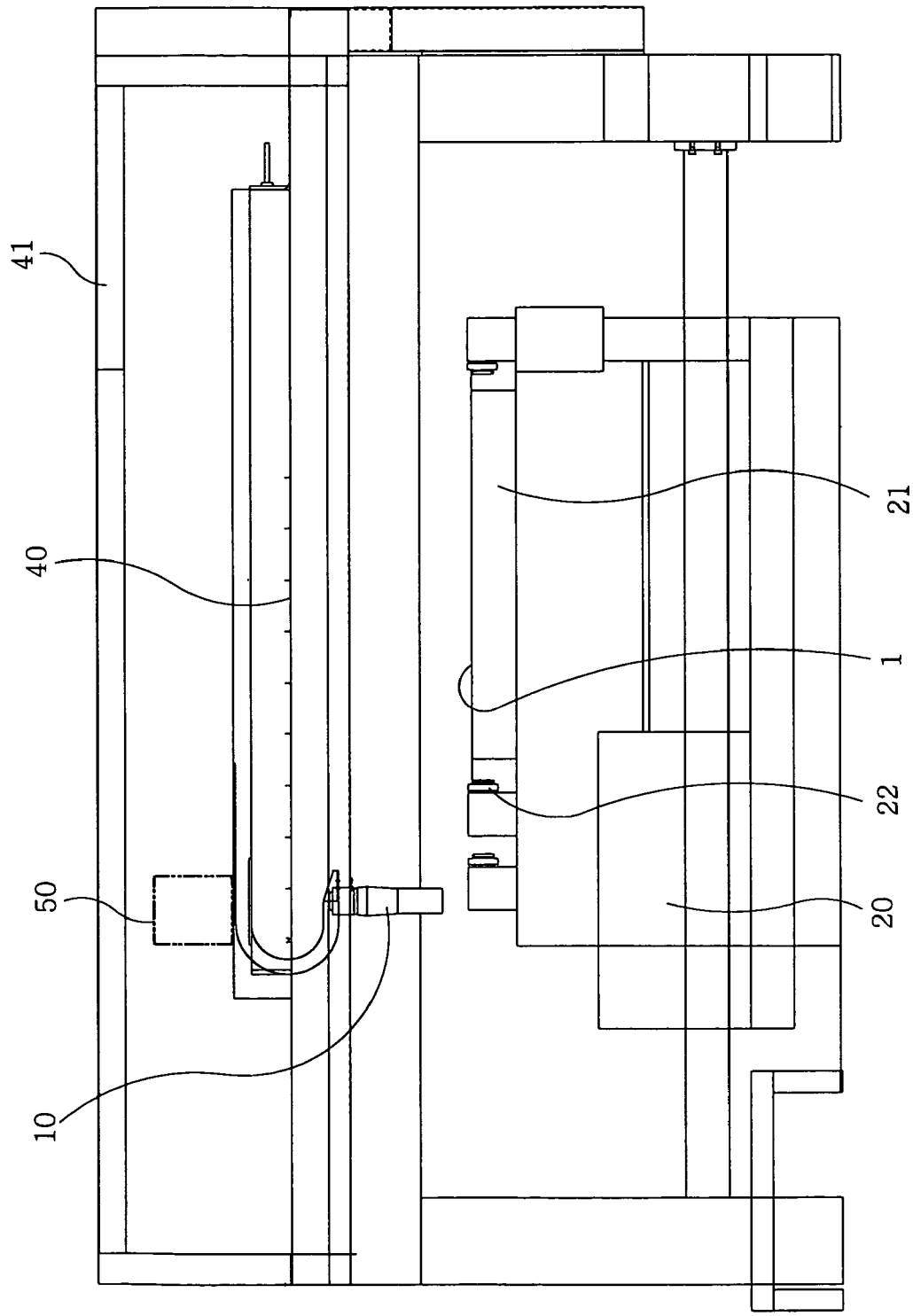
FIG. 2 shows a front view of an apparatus to perform a method for measuring particles in a glass substrate in accordance with the present invention.

Referring to FIGS. 1A, 1B and 2, a method for measuring particles in a glass substrate in accordance with the present invention is a method for measuring information on particles P, i.e., a number, positions, sizes, and the like, in a glass substrate 1, which includes the following steps: step S10 wherein a plurality of glass substrates 1 are conveyed sequentially; step S20 wherein information on the particles P residing in a unit area of the glass substrate 1 scanned by a camera 10 is stored as data, the camera 10 maintaining a desired distance from the glass substrate 1; step S30 wherein, while maintaining the desired distance from the glass substrate 1, the camera 10 is moved a preset distance, e.g., a scan width of the camera 10, in a direction perpendicular to the travel path of the glass substrate 1; step S40 wherein, after scanning the following glass substrate 1 by the camera 10, information on the particles P residing in a unit area of the glass substrate 1 is stored; and step S50 wherein, if a sum of the unit areas of the glass substrates 1 scanned by the camera 10 is within an allowed limit of the area of one glass substrate 1, information on the particles P in the entire glass substrate 1 is obtained and stored by summing up the information on the particles P residing in the respective scanned unit areas.

At step S10, a plurality of glass substrates 1 entering a clean room after being washed are conveyed sequentially. The glass substrates 1 are conveyed by rollers 22 arranged at both sides of a floating table 20, being floated by air jets coming out of a plurality of floating bars 21 arranged on the floating table 20.

Since the plurality of glass substrates 1 are conveyed by being floated by air jets, vibration of the glass substrate 1 is minimized. Consequentially, the camera 10 obtains a clear image of the glass substrate 1.

At step S20, information on the particles P residing in a unit area is stored, wherein the information is obtained by scanning the glass substrate 1 in a longitudinal direction, i.e., the travel direction of the glass substrate 1, while the glass substrate 1 passes by the camera 10; and the camera 10 is arranged over the travel path of the glass substrate and has a preset scan width.

Figure 3:
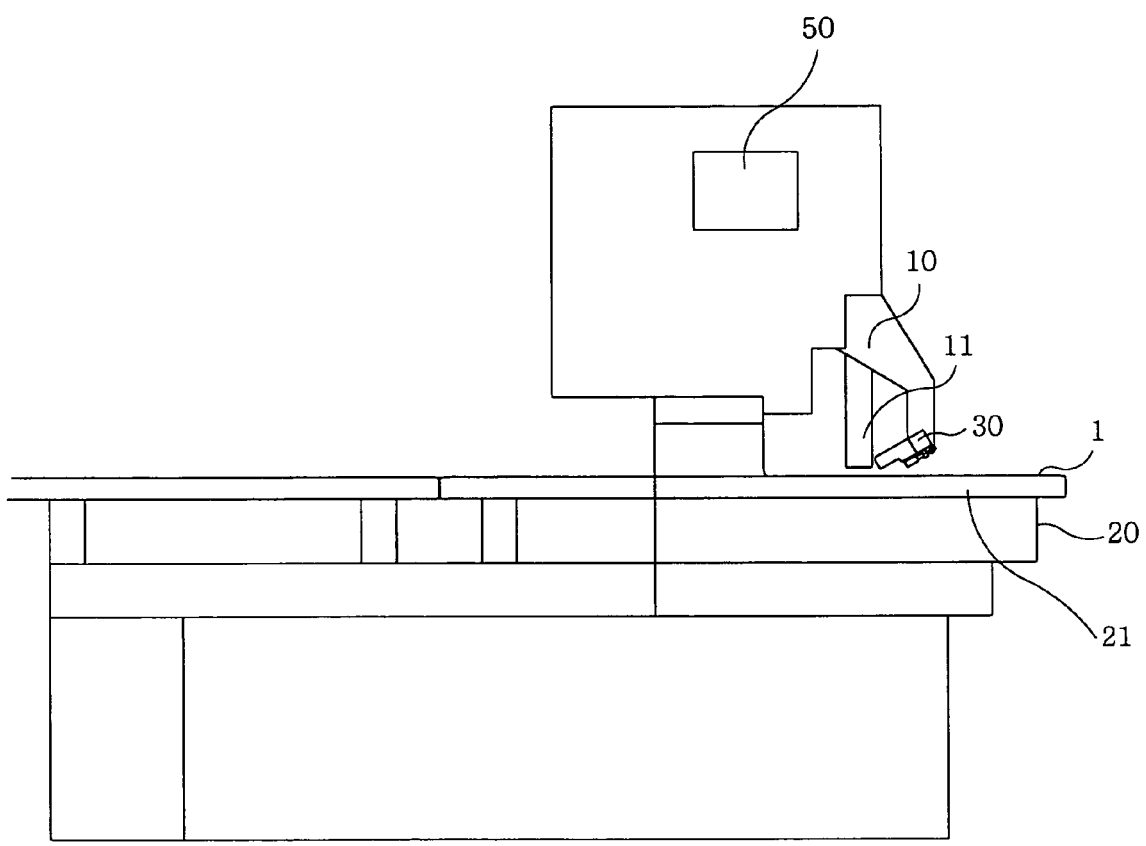
FIG. 3 illustrates a side view of an apparatus to perform a method for measuring particles in a glass substrate in accordance with the present invention.

Referring to FIG. 3, the camera 10 is a line scan camera, which scans a unit area corresponding to the preset scan width. At a lower part of the camera 10 is installed a lens 11, beside which is arranged an illumination 30, e.g., a halogen lamp, which illuminates the area to be photographed.

The camera 10 is arranged, while maintaining a desired distance from the glass substrate 1, to move along a guide rail 40 which is installed inside a frame 41 positioned above the glass substrate 1 to be perpendicular to the travel path of the glass substrate 1. Since the camera 10 is joined mechanically with a linear motor 50 which moves along the guide rail 40, the camera 10 moves along the guide rail 40, together with the illumination 30, when the linear motor 50 is driven.

Figure 4:
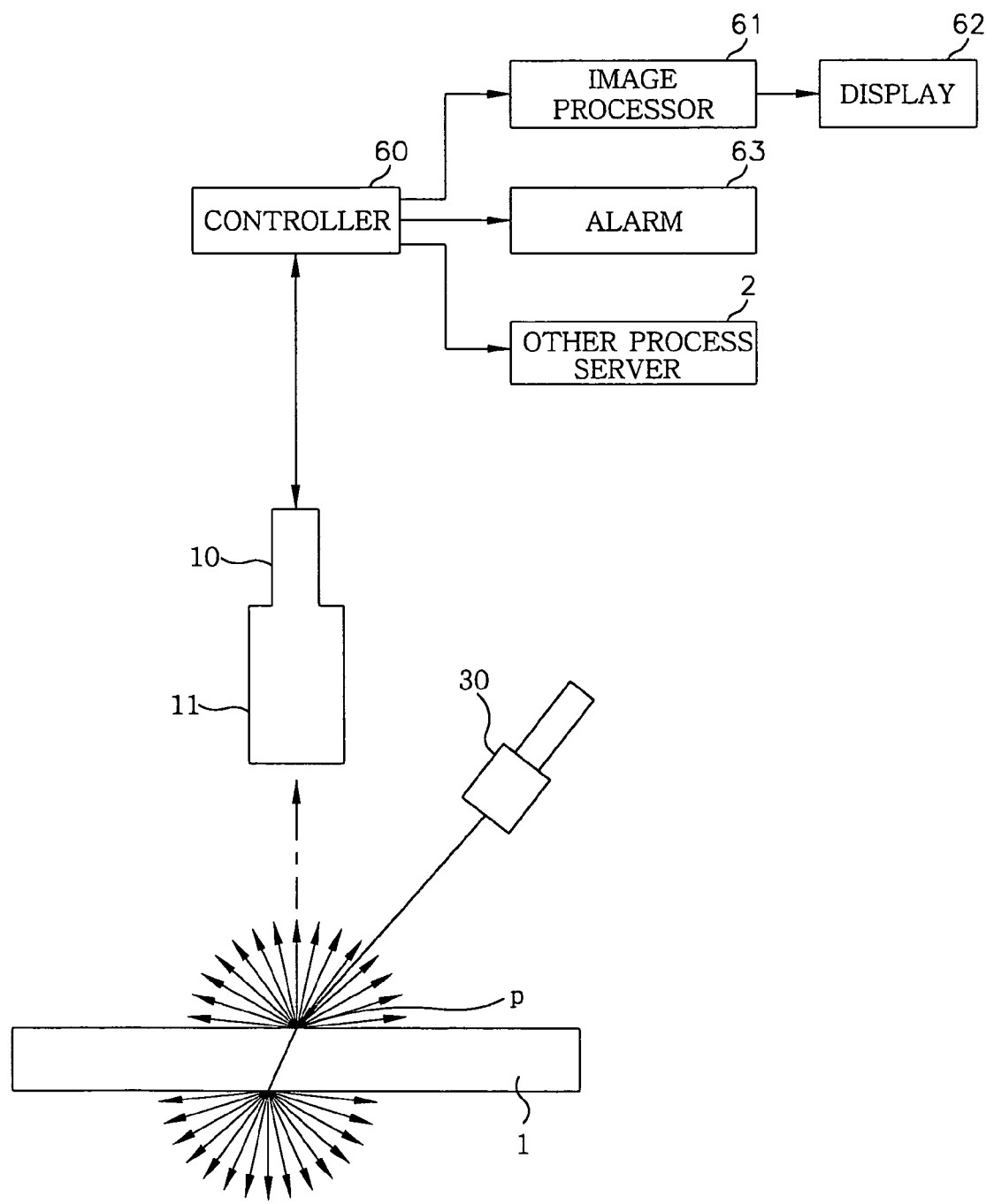
FIG. 4 depicts a construction of an apparatus to perform a method for measuring particles in a glass substrate in accordance with the present invention.

Referring to FIG. 4, as the camera 10 scans a unit area of the glass substrate 1 conveyed below the camera 10 with a preset scan width, an image of the scanned unit area is sent to a controller 60 and information on the particles P, i.e., a number, sizes, positions, and the like, in the image of the scanned unit area is processed by an image processor 61 and stored.

The information on the particles P in the unit area of the glass substrate 1 may be displayed outside through a display 62 so that the information can be understood easily from the outside.

At step S60, from the information on the particles in the unit area of the glass substrate 1, it is estimated whether the number of the particles P is equal to or larger than the preset number. And if the number of the particles P is equal to or larger than the preset number, at step S90, an alarm 63 raises an alarm to the outside.

The alarm 63 may be a text or an image which gives an alarm on the display 62, a speaker which sounds an alarm outside, a blinker, and the like. The alarm 63 may be installed in a place where the particles in a glass substrate 1 are inspected, a place for a former process, i.e., a washing process, or other places in order to influence the other processes by warning of an excessive generation of the particles P in the glass substrate 1.

At step S60, if the number of the particles P is less than the preset number, step S30 is executed, wherein, while maintaining the desired distance from the glass substrate 1, the camera 10 is moved a preset distance in a direction perpendicular to the travel path of the glass substrate 1.

At step S30, the camera 10 moves a preset distance along the guide rail 40 in a direction perpendicular to the travel path of the glass substrate 1, together with the linear motor 50, through an operation of the linear motor 50. Accordingly, the camera 10 is positioned to scan a unit area neighboring the scanned unit area.

When the camera 10 is positioned to scan the new unit area of a newly introduced glass substrate 1 which neighbors the scanned unit area, step S40 is executed.

At step S40, information on the particles P residing in the new unit area is stored, wherein the information is obtained by scanning the newly introduced glass substrate 1 by the camera which is moved a preset distance in a direction perpendicular to the travel path of the glass substrate 1.

The information on the particles P in the unit area of the new glass substrate 1 may be displayed outside through the display 62 so that the information on the particles P in the unit area of the glass substrate 1, i.e., a number, sizes, positions, and the like, can be understood easily from the outside.

Figure 5:
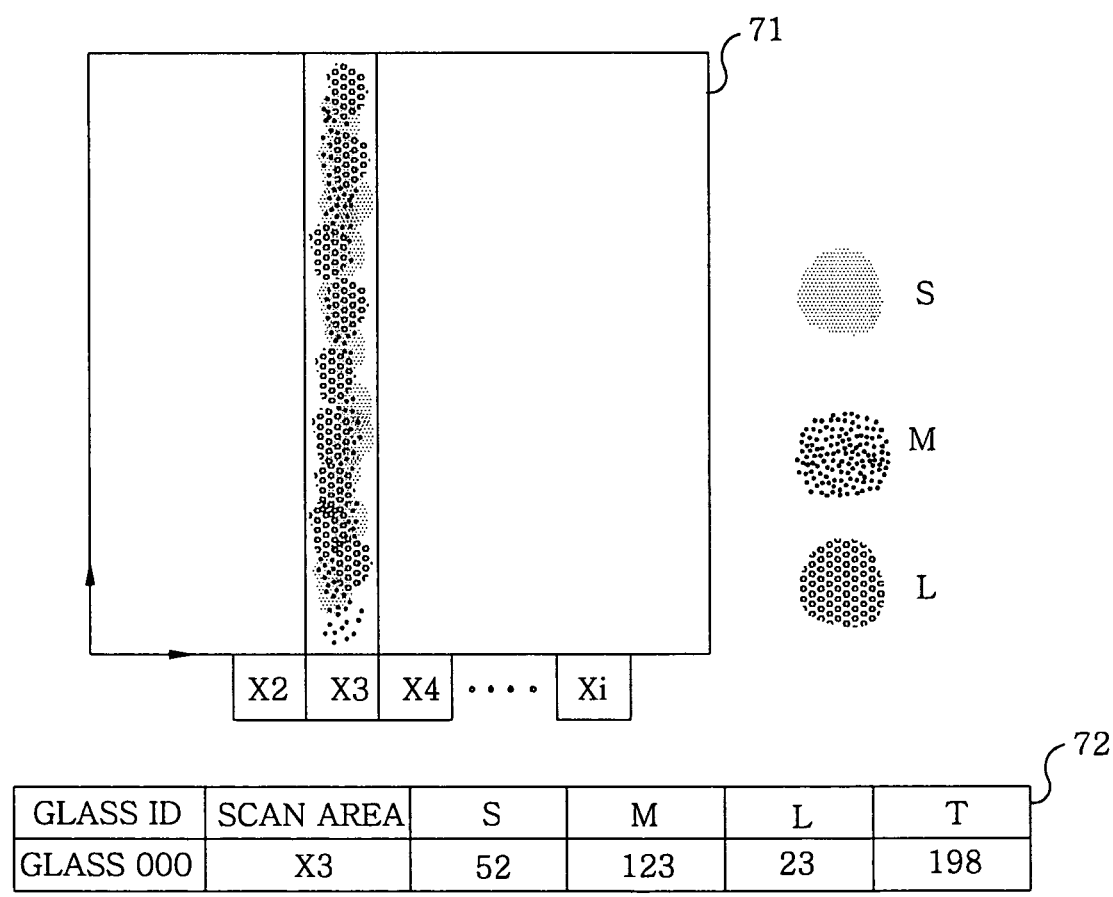
FIG. 5 represents a scanned result obtained by using a method for measuring particles in a glass substrate in accordance with the present invention.

FIG. 5 shows a data format of the result obtained by performing a scan of the unit area using the camera 10, which includes a map 71 showing positions and distribution of the particles P obtained by scanning a unit area X3; and a table 72 showing numbers of the particles P in the unit area X3 classified by a particle size (S, M and L). Other than this, the data format can be displayed in various forms.

The particle size is classified into 3 groups, wherein the size grows in order of S(small), M(medium) and L(large).

At step S70, from the information on the particles P in the unit area of the new glass substrate 1, it is estimated whether the number of the particles P is equal to or larger than the preset number. If the number of the particles P is equal to or larger than the preset number, at step S90, the alarm 63 raises an alarm to the outside. And if not, the following step S51 is executed.

At step S51, it is estimated whether a sum of the respective unit areas which were scanned during repetition of steps S30 and S40 is within an allowed limit of the area of one glass substrate 1. If the sum is within the allowed limit, by summing up the information on the particles P residing in the respective scanned unit areas, information on the particles P in the entire glass substrate 1 is obtained and stored. This data may be displayed outside as sampling information on the particles P in the entire area of the glass substrate 1.

The data displayed as information on the particles P in the entire area of the glass substrate 1 is statistical data on the plurality of glass substrates 1 scanned by the camera 10 until the sum of the scanned unit areas reaches the allowed limit of the area of a glass substrate 1.

At step S51, whether the sum of the respective unit areas of the glass substrates 1 is within the allowed limit of the area of a glass substrate 1 or not is estimated by following ways: obtaining a scanning number of the camera 10 by comparing the width of the glass substrate 1 with the scan width of the camera 10; and figuring out when the sum of the respective unit areas of the glass substrates 1 approaches most closely to the area of a glass substrate 1.

At step S80, it is estimated whether the number of the particles P is equal to or larger than the preset number by using the information on the particles P in the entire area of the glass substrate 1 which is obtained at step S50. If the number of the particles P is equal to or larger than the preset number, the alarm 63 raises an alarm to the outside at step S90. And if not, the above-described procedure is terminated.

Referring to FIG. 4, information on the particles P in the respective unit areas of the glass substrates 1 and that in the entire area of the glass substrate 1 may be sent to other process servers 2 and displayed outside so that a succeeding measures can be taken to reduce generation of particles P in the glass substrate 1.

A method for measuring particles in a glass substrate described-above operates in a following sequence.

At step S10, a plurality of glass substrates 1 entering the clean room after being subjected to a washing process is floated by air jets and conveyed sequentially at regular intervals. When a sensor (not shown) detects a glass substrate 1 entering the clean room, the camera 10 arranged over the travel path of the glass substrate 1 scans a unit area in a longitudinal direction, i.e., the direction of travel path, with a regular scan width.

At step S20, information on the particles P, i.e., a number, sizes, positions, and the like, is obtained and stored from the unit area of glass substrate 1 scanned by camera 10. And this data may be displayed outside through the display 62.

At step S60, it is estimated whether the number of the particles P is equal to or larger than the preset number from the information on the particles P in the scanned unit area of the glass substrate 1. If the answer is "Yes", i.e., if the number of the particles P is equal to or larger than the preset number, the alarm 63 raises an alarm to the outside at step S90. And if the answer is "No", i.e., if the number of the particles P is less than the preset number, step S30 is executed to move the camera 10 in a direction perpendicular to the travel path of the glass substrate 1. That is, when the linear motor 50 is driven, the camera 10, together with the linear motor 50, is moved along the guide rail 40 in a direction perpendicular to the travel path of the glass substrate 1 such that it will be positioned to scan a unit area neighboring the scanned unit area.

At step S40, information on the particles P residing in the new unit area which is obtained by scanning the newly introduced glass substrate 1 is stored. And the data may be displayed outside through the display 62.

At step S70, from the information on the particles P in the unit area of the new glass substrate 1, it is estimated whether the number of the particles P is equal to or larger than the preset number. If the number of the particles P is equal to or larger than the preset number, the alarm 63 raises an alarm to outside at step S90. And if not, the following step S51 is executed, wherein it is estimated whether the sum of the respective unit areas which were scanned during repetition of steps S30 and S40 is within the allowed limit of the area of a glass substrate 1.

At step S51, if the answer is "No", i.e., if the sum is not within the allowed limit, steps S30 and S40 are repeated again. And if the answer is "Yes", i.e., if the sum is within the allowed limit, at step S50, information on the particles P in the entire glass substrate 1 is obtained and stored by summing up information on the particles P residing in the respective scanned unit areas.

The sampling data displayed as information on the particles P in the entire area of the glass substrate 1 is used as statistical data of the plurality of glass substrates 1 scanned by the camera 10 until the sum of the scanned unit areas falls within the allowed limit of the area of a glass substrate 1.

When the data is displayed outside as information on the particles P in the entire area of the glass substrate 1 scanned by the camera 10, at step S80, it is estimated whether the number of the particles P is equal to or larger than the preset number. At step S90, if the number is equal to or larger than the preset number, the alarm 63 raises an alarm to outside.

The information on the particles P in the respective unit areas of the glass substrates 1 and that in the entire area of the glass substrate 1 may be sent to other process servers 2, e.g., the washing process, and displayed outside so that a succeeding measures can be taken to reduce generation of particles P in the glass substrate 1.

As described above, by obtaining and storing information on the particles P in the respective unit areas and in the entire area of the glass substrates 1 scanned by the camera 10, and displaying the information as a statistic, a method for measuring particles in a glass substrate in accordance with the present invention is capable of providing sampling information on the particles in a glass substrate without interruption in the process line; utilizing a clean room space efficiently; and performing an inspection of a large-sized glass substrate.

While the invention has been shown and described with respect to the preferred embodiments, it will be understood by those skilled in the art that various changes and modifications may be made without departing from the spirit and scope of the invention as defined in the following claims.

What is claimed is:

1. A method for measuring particles in a glass substrate, comprising the steps of:
    (a) sequentially conveying a plurality of glass substrates;
    (b) scanning with a camera a unit area of a glass substrate in a direction of a travel path of the glass substrate and storing particle information thereof, wherein the camera is placed above a travel path of the glass substrates and a scan width thereof is preset;
    (c) shifting the camera in a direction perpendicular to the travel path of the glass substrate to a position corresponding to a next unit area for a succeeding glass substrate;
    (d) storing information on the particles in the unit area of the succeeding glass substrate obtained by scanning the glass substrate using the shifted camera;
    (e) estimating whether a sum of the respective scanned unit areas is within an allowed limit of an area of a glass substrate; and
    (f) returning to step (c) if an answer from step (e) is "No" or storing information on the particles in the entire glass substrate obtained by summing up the information on the particles in the respective scanned unit areas if the answer is "Yes".

2. The method of claim 1, wherein the plurality of glass substrates is conveyed by being floated by air jets.

3. The method of claim 1, further comprising the step of displaying the information stored at steps (b), (d) and/or (f).

4. The method of claim 1, further comprising the step of notifying a user if a number of particles measured at step (b) and/or (d) is equal to or larger than a preset number.

5. The method of claim 1, further comprising the step of notifying a user if the number of particles estimated for an entire area of the glass substrate obtained at step (f) is equal to or greater than a preset number.

* * * * *